United States Patent [19]

Chang et al.

[11] 4,344,868
[45] Aug. 17, 1982

[54] CATALYST FOR SYNTHESIS GAS CONVERSION TO OXYGENATES

[75] Inventors: Clarence D. Chang, Princeton; William H. Lang, Pennington, both of N.J.

[73] Assignee: Mobil Oil Corporation, New York, N.Y.

[21] Appl. No.: 137,943

[22] Filed: Apr. 7, 1980

Related U.S. Application Data

[63] Continuation-in-part of Ser. No. 65,821, Aug. 13, 1979, abandoned.

[51] Int. Cl.$^3$ .............................................. B01J 29/32
[52] U.S. Cl. ................................. 252/455 Z; 518/715
[58] Field of Search .................... 252/455 Z; 260/449; 518/715

[56] References Cited

U.S. PATENT DOCUMENTS 4,157,338  6/1979  Haag et al. ..................... 260/449 M
4,172,843  10/1979  Dwyer et al. .................. 252/455 Z
4,218,573  8/1980  Tabak et al. ................... 252/455 Z Primary Examiner—Carl F. Dees
Attorney, Agent, or Firm—Charles A. Huggett; Michael G. Gilman; Malcolm D. Keen

[57] ABSTRACT

The conversion of synthesis gas comprising hydrogen and carbon oxides to form oxygenate-containing mixtures which are limited compositionally in being virtually free of $C_{11}+$ compounds, with a zeolite which is virtually free of acid sites and characterized by a silica to alumina mole ratio of at least about 12 and a constraint index within the range of 1 to 12, having intimately combined therewith a metal selected from the group consisting of rhodium, platinum, palladium and iridium.

12 Claims, No Drawings

CATALYST FOR SYNTHESIS GAS CONVERSION TO OXYGENATES

CROSS-REFERENCE TO RELATED APPLICATION

This is a continuation-in-part of application Ser. No. 065,821 filed Aug. 13, 1979 now abandoned.

BACKGROUND OF THE INVENTION

1. Field of the Invention

This invention is concerned with a process for converting synthesis gas comprising hydrogen and carbon oxides to form a product comprising a substantial proportion of organic oxygenates. In one aspect, this invention is concerned with a process for converting synthesis gas comprising hydrogen and carbon oxides to form mixtures of oxygenates and hydrocarbons, which are limited compositionally in being virtually free of $C_{11}+$ compounds. In another aspect, this invention is concerned with providing a novel catalyst composition for the conversion of synthesis gas to a product comprising a substantial proportion of organic oxygenates, which is limited compositionally in being virtually free of $C_{11}+$ compounds.

2. Prior Art

Processes for the conversion of coal and other hydrocarbons such as natural gas to a gaseous mixture consisting essentially of hydrogen and carbon monoxide, or of hydrogen and carbon dioxide, or of hydrogen and carbon monoxide and carbon dioxide, are well known. Although various processes may be employed for the gasification of carbonaceous fuels, those of major importance depend either on the partial combustion of the fuel with an oxygen-containing gas or on the high temperature reaction of the fuel with steam, or on a combination of these two reactions. An excellent summary of the art of gas manufacture, including synthesis gas, from solid and liquid fuels, is given in the ENCYCLOPEDIA OF CHEMICAL TECHNOLOGY, Edited by Kirk-Othmer, Second Edition, Volume 10, pages 353-433 (1966), Interscience Publishers, New York, N.Y., the contents of which are herein incorporated by reference. The techniques for gasification of coal or other solid, liquid or gaseous fuel are not considered to be per se inventive here.

It would be very desirable to be able to effectively convert synthesis gas, and thereby coal and natural gas, to highly valued fuels such as motor gasoline with high octane number and chemical intermediates. It is well known that synthesis gas will undergo conversion to form reduction products of carbon monoxide, such as hydrocarbons and alcohols, at from about 300° F. to about 850° F. under pressure from about 1 to 1000 atmospheres, over a fairly wide variety of catalysts. The Fischer-Tropsch process, for example, which has been most extensively studied, produces a range of liquid hydrocarbons, a portion of which have been used as low octane gasoline. The types of catalysts that have been studied for this and related processes include those based on metals or oxides of zinc, iron, cobalt, nickel, ruthenium, thorium, rhodium and osmium.

Catalysts based on ZnO are particularly suited for the production of methanol and dimethyl ether. Catalysts based on Fe, Co, and Ni, and especially Fe, are particularly suited for the production of oxygenated and hydrocarbon products that have at least one carbon-to-carbon bond in their structure. With the exception of ruthenium, all practical synthesis catalysts contain chemical and structural promoters. These promoters include copper, chromia, alumina and alkali. Alkali is of particular importance with iron catalysts, since it greatly enhances the conversion efficiency of the iron catalyst. Supports such as kieselguhr sometimes act beneficially.

The catalyzed reduction of carbon monoxide or carbon dioxide by hydrogen produces various oxygenated and hydrocarbon products, depending on the particular catalyst and reaction conditions chosen. The products that are formed include methanol; dimethyl ether; acetone; acetic acid; normal propyl alcohol; higher alcohols; methane; gaseous, liquid and solid olefins and paraffins. It should be noted that this spectrum of products consists of aliphatic compounds; aromatic hydrocarbon either are totally absent or are formed in minor quantities.

In general, when operating at the lower end of the temperature range, i.e. from about 300° F. to about 500° F., in the reduction of carbon monoxide, and with pressures greater than about 20 atmospheres, thermodynamic considerations suggest that aliphatic hydrocarbons are likely to form in preference to their aromatic counterparts. Furthermore, in some catalytic systems it has been noted that aromatic hydrocarbon impurities in the synthesis gas inactivate the synthesis catalyst, and one may speculate that a number of known synthesis catalysts intrinsically are not capable of producing aromatic hydrocarbons.

The wide range of catalysts and catalyst modifications disclosed in the art and an equally wide range of conversion conditions for the reduction of carbon monoxide by hydrogen provide considerable flexibility toward obtaining selected boiling range products. Nonetheless, in spite of this flexibility, it has not proved possible to make such selections so as to produce oxygenates or mixtures of oxygenates and hydrocarbons which are limited compositionally in being virtually free of $C_{11}+$ compounds. A review of the status of this art is given in *Carbon Monoxide-Hydrogen Reactions*, ENCYCLOPEDIA OF CHEMICAL TECHNOLOGY, Edited by Kirk-Othmer, Second Edition, Volume 4, pages 446-488, Interscience Publishers, New York, N.Y., the text of which is incorporated herein by reference.

Recently it has been discovered that synthesis gas may be converted to oxygenated organic compounds and these then converted to higher hydrocarbons, particularly high octane gasoline, by catalytic contact of the synthesis gas with a carbon monoxide reduction catalyst followed by contacting the conversion products so produced with a special type of zeolite catalyst in a separate reaction zone. This two-stage conversion is described in U.S. Pat. No. 4,076,761.

Another process to produce high octane gasoline is disclosed in U.S. Pat. No. 3,972,958. In this process, coal is gasified and the resultant synthesis gas from the gasification is converted into high octane aromatic gasoline and light hydrocarbon gases.

The conversion of synthesis gas to hydrocarbon mixtures is described in U.S. Pat. Nos. 4,086,252 and 4,096,163. These patents involve the use of acidic crystalline zeolites in admixture with carbon oxide reducing components, such as Fischer-Tropsch catalysts. Conversion of synthesis gas to hydrocarbon mixtures is also described in U.S. Pat. No. 4,157,338.

Copending U.S. patent application Ser. No. 926,987 filed July 21, 1978, now U.S. Pat. No. 4,172,843, describes conversion of syngas to olefinic naphtha utilizing a catalyst comprising an iron containing Fischer-Tropsch Component and a substantially non-acidic ZSM-5 type zeolite.

Compositions of iron, cobalt or nickel deposited in the inner absorption regions of crystalline zeolites are described in U.S. Pat. No. 3,013,990. Attempts to convert synthesis gas over X-zeolite base exchanged with iron, cobalt and nickel are described in Erdoel und Kohle—ERDGAS, PETROCHEMIE: BRENNSTOFF—CHEMIE, Volume 25, No. 4, pages 187-188, April 1972.

It is an object of the present invention to provide an improved process for converting fossil fuels to mixtures of hydrocarbons and oxygenates containing large quantities of high desirable constituents. It is a further object of this invention to provide a more efficient method for converting a mixture of gaseous carbon oxides and hydrogen to form a product comprising a substantial proportion of organic oxygenates. It is a further object of this invention to provide an improved method for converting synthesis gas to mixtures of hydrocarbons and oxygenates which are virtually free of $C_{11}+$ compounds. It is a further object of this invention for converting synthesis gas to high octane gasoline and oxygenates which may be valuable as chemical intermediates. It is a further object of this invention to provide novel catalysts for the conversion of synthesis gas.

SUMMARY OF THE INVENTION

It has now been discovered that valuable oxygenate containing mixtures can be produced by reacting synthesis gas, i.e., mixtures of hydrogen gas with gaseous carbon oxides, or the equivalents of such mixtures, in the presence of certain catalysts. The catalysts, as will be more fully described hereinafter, are those in which a novel class of zeolites characterized by a silica to alumina mole ratio of at least 12 and a constraint index within the range of 1 to 12 and which is virtually free of acid sites (i.e. substantially non-acidic) and having intimately combined therewith a metal selected from the group consisting of rhodium, platinum, palladium and iridium, preferably rhodium.

Depending on the catalyst and the particular reaction conditions, one may obtain substantial quantities of liquid mixtures which are rich in oxygenates and are limited compositionally in being virtually free of $C_{11}+$ compounds and thus eminently suited for use as a high octane gasoline or chemical intermediate. Oxygenate products so obtained comprise alcohols, esters, ketones, aldehydes and acids.

DETAILED DESCRIPTION AND PREFERRED EMBODIMENTS

Synthesis gas for use in this invention consists of a mixture of hydrogen gas with gaseous carbon oxides, including carbon monoxide and carbon dioxide. By way of illustration, a typical purified synthesis gas will have the composition, on a water-free basis, in volume percentages, as follows: hydrogen 51; carbon monoxide, 40; carbon dioxide, 4; methane, 1; and nitrogen, 4.

The synthesis gas may be prepared from fossil fuels by any of the known methods, including such in-situ gasification processes as the underground partial combustion of coal and petroleum deposits. The term "fossil fuels", as used herein, is intended to include anthracite and bituminous coal, lignite, crude petroleum, shale oil, oil from tar sands, natural gas, as well as fuels derived from simple physical separations or more profound transformations of these materials, including coked coal, petroleum coke, gas oil, residua from petroleum distillation, and two or more of any of the foregoing materials in combination. Other carbonaceous fuels such as peat, wood and cellulosic waste materials also may be used.

The raw synthesis gas produced from fossil fuels will contain various impurities such as particulates, sulfur, ammonia and metal carbonyl compounds, and will be characterized by hydrogen-to-carbon oxides ratios which will depend on the fossil fuel and the particular gasification technology utilized. In general, it is desirable for the efficiency of the subsequent conversion steps to purify the raw synthesis gas by the removal of impurities. Techniques for such purification are known and are not part of this invention. Furthermore, it may be required to adjust the hydrogen-to-carbon oxides volume ratio to be within a preferred range prior to use in this invention. Should the purified synthesis gas be excessively rich in carbon oxides, it may be brought within the preferred range by the well known water-gas shift reaction. On the other hand, should the synthesis gas be excessively rich in hydrogen, it may be adjusted into the preferred range by the addition of carbon dioxide or carbon monoxide.

It is contemplated that the synthesis gas for use in this invention includes art-recognized equivalents to the already-described mixtures of hydrogen gas with gaseous carbon oxides. Mixtures of carbon monoxide and steam, for example, or of carbon dioxide and hydrogen, to provide adjusted synthesis gas by in-situ reaction, are contemplated.

The catalysts of this invention comprise a novel class of zeolites which is virtually free of acid sites, i.e. substantially non-acidic, having intimately combined therewith a metal selected from the group consisting of rhodium, platinum, palladium and iridium, with rhodium being particuarly preferred. The novel class of zeolites of this invention is characterized by a silica to alumina mole ratio of at least 12 and a constraint index, as defined hereinafter, within the range of 1 to 12.

An important characteristic of the crystal structure of this novel class of zeolites is that it provides constrained access to, and egress from, the intracrystalline free space by virtue of having a pore size intermediate between the small pore Linde A and the large pore Linde X, i.e. the pore windows of the structure are of about a size such as would be provided by ten-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon or aluminum atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is preferred in many instances to use zeolites having much higher silica to alumina mole ratios. In addition, zeolites as otherwise characterized herein but which are substantially free of aluminum, i.e. having high silica to alumina mole ratios which range up to and including infinity, are found to be useful and even preferable in some instances. Such "high silica" or "highly siliceous" zeolites are intended to be included within this description. The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by eight-membered rings of silicon and aluminum atoms, then access to molecules of larger cross-section than normal hexane is excluded and the zeolite is not of the desired type. Windows of ten-membered rings are preferred, although excessive puckering or pore blockage may render these catalysts ineffective. Twelve-membered rings do not generally appear to offer sufficient constraint to produce the advantageous conversions desired in the instant invention, although structures can be conceived, due to pore blockage or other cause, that may be operative.

Rather than attempt to judge from crystal structure whether or not a zeolite possesses the necessary constrained access, a simple determination of the "Constraint Index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most samples and represents preferred conditions, it may occasionally be necessary to use somewhat more severe conditions for samples of very low activity, such as those having a very high silica to alumina mole ratio. In those instances, a temperature of up to about 1000° F. and a liquid hourly space velocity of less than one, such as 0.1 or less, can be employed in order to achieve a minimum total conversion of about 10%.

There also may be situations where the activity is so low, i.e. silica to alumina mole ratio approaching infinity or zeolites with virtually no acid sites, that the constraint index cannot be adequately measured, if at all. In such situations, Constraint Index is meant to mean the Constraint Index of the exact same substance (i.e. same crystal structure as determined by such means as X-ray diffraction pattern), but in a measureable form (i.e. acid or aluminum containing form).

The "Constraint Index" is calculated as follows:

$$\text{Constraint Index} = \frac{\log_{10} (\text{fraction of n-hexane remaining})}{\log_{10} (\text{fraction of 3-methylpentane remaining})}$$

The Constraint Index approximates the ratio of the cracking rate constants for the two hydrocarbons. Zeolites suitable for the present invention are those having a Constraint Index from about 1.0 to 12.0. Constraint Index (C.I.) values for some typical zeolites, including some not within the scope of this invention, are:

|  | C.I. |
|---|---|
| ZSM-4 | 0.5 |
| ZSM-5 | 8.3 |
| ZSM-11 | 8.7 |
| ZSM-12 | 2.0 |
| ZSM-23 | 9.1 |
| ZSM-35 | 4.5 |
| ZSM-38 | 2.0 |
| TMA Offretite | 3.7 |
| Beta | 0.6 |
| ZSM-4 | 0.5 |
| Acid Mordenite (H-Zeolon) | 0.5 |
| REY | 0.4 |
| Amorphous Silica-Alumina | 0.6 |
| Erionite | 38 |
| Clinoptilolite | 3.4 |

The above-described Constraint Index is an important and even a critical definition of those zeolites which are useful to catalyze the instant process. The very nature of this parameter and the recited technique by which it is determined, however, admit of the possibility that a given zeolite can be tested under somewhat different conditions and thereby have different Constraint Indexes. Constraint Index seems to vary somewhat with severity of operation (conversion) and the presence or absence of binders. Likewise, other variables such as crystal size of the zeolite, the presence of occluded contaminants, etc., may affect the Constraint Index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12.

Thus, it should be understood that "Constraint Index" as such value is used herein is an inclusive rather than an exclusive value. That is, a zeolite when tested by any combination of conditions within the testing definition set forth hereinabove to have a constraint index of about 1 to 12 is intended to be included in the instant novel zeolite definition regardless that the same identical crystalline zeolite tested under other defined conditions may give a Constraint Index value outside of the range of 1 to 12.

In a preferred aspect of this invention, the zeolites useful herein are selected as those having a crystal framework density, in the dry hydrogen form, of not substantially below about 1.6 grams per cubic centimeter. It has been found that zeolites which satisfy all three of these criteria are most desired. Therefore, the preferred catalysts of this invention are those comprising zeolites having a Constraint Index as defined above of about 1 to 12, a silica to alumina mole ratio of at least about 12 and a dried crystal density of not substantially less than about 1.6 grams per cubic centimeter. The dry density for known structures may be calculated from the number of silicon plus aluminum atoms per 1000 cubic Angstroms, as given, e.g., on page 19 of the article on *Zeolite Structure* by W. M. Meier. This paper, the entire contents of which are incorporated herein by reference, is included in *Proceedings of the Conference on Molecular Sieves, London, April* 1967, published by the Society of Chemical Industry, London, 1968. When the crystal structure is unknown, the crystal framework density may be determined by classical pycnometer techniques. For example, it may be determined by immersing the dry hydrogen form of the zeolite in an organic solvent which is not sorbed by the crystal. It is possible that the unusual sustained activity and stability of this class of zeolites are associated with its high crystal anionic framework density of not less than about 1.6 grams per cubic centimeter. This high density of course must be associated with a relatively small amount of free space within the crystal, which might be expected to result in more stable structures. This free space, however, seems to be important as the locus of catalytic activity.

Crystal framework densities of some typical zeolites, including some which are not within the purview of this invention, are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | — | 1.79 |
| ZSM-23 | — | 1.80 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

The novel class of zeolites defined herein is exemplified by ZSM-5, ZSM-11, ZSM-12, ZSM-23, ZSM-35, ZSM-38 and other similar materials.

ZSM-5 is more particularly described in U.S. Pat. No. 3,702,886, the entire contents of which are incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-23 is more particularly described in U.S. Pat. No. 4,076,842, the entire contents of which are incorporated herein by reference.

ZSM-35 is more particularly described in U.S. Pat. No. 4,016,245, the entire contents of which are incorporated herein by reference.

ZSM-38 is more particularly described in U.S. Pat. No. 4,046,859, the entire contents of which are incorporated herein by reference.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica to alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific crystalline zeolites described, when prepared in the presence of organic cations, are substantially inactive, possibly because the intracrystalline free space is occupied by organic cations from the forming solution. They may be activated by heating in an inert atmosphere at 1000° F. for 1 hour, for example, followed by base exchange with ammonium salts, followed by calcination at 1000° F. in air. The presence of organic cations in the forming solution may not be absolutely essential to the formation of this special type zeolite; however, the presence of these cations does appear to favor the formation of this special type of zeolite. More generally, it is desirable to activate this type zeolite by base exchange with ammonium salts, followed by calcination in air at about 1000° F. for from about 15 minutes to about 24 hours.

Natural zeolites may sometimes be converted to this type zeolite by various activation procedures and other treatments such as base exchange, steaming, alumina extraction and calcination, alone or in combinations. Natural minerals which may be so treated include ferrierite, brewsterite, stilbite, dachiardite, epistilbite, heulandite and clinoptilolite.

The instant invention is concerned with a substantially non-acidic zeolite which is virtually free of acidic sites. Without wishing to be bound by any particular theory of operability, it is believed that the usefulness of substantially non-acidic zeolites lies in their ability to influence the selectivity or course of reactions by taking advantage of the particular pore diameters of the zeolite. Thus, this invention is not at all concerned with conventional acidic zeolite catalysis, but rather relies on the sieving function of zeolites.

There are various ways in order to arrive at a zeolite which is virtually free of acidic sites. One way to arrive at a substantially non-acidic zeolite is to use a high-silica zeolite. It is known in the art that the greater the aluminum content of a zeolite which is present in the skeletal structure, the greater the opportunity there is to have exchangeable sites which can be acidic. Conversely, the lower the aluminum content, the less availability there is to provide acid sites via base exchange or other techniques. The zeolite component of the catalyst of this invention which is substantially free of alumina may contain minor amounts of such oxide attributable primarily to the presence of aluminum impurities in the reactants, the atmosphere, and/or the equipment employed in preparing them. Preparation of a high silica material which may be employed herein is described in U.S. Pat. No. 3,941,871, the entire contents of which is incorporated by reference herein. That patent provides a family of materials which are essentially free of the metals of Group III, e.g. aluminum, gallium, and are characterized by an X-ray diffraction pattern characteristic of ZSM-5.

A technique that can be applied to the novel class of zeolites of the present invention to arrive at a substantially non-acidic zeolite is to neutralize an acidic zeolite by means of base exchange. Such base exchange can be accomplished with cations from the group consisting of the metals of Group IA of the Periodic Chart of the Elements (Fisher Scientific Company, Cat. No. 5-702-10, 1978), i.e. Li, Na, K, Rb, Cs, Fr, preferably Na. Also base exchange can be carried out with the elements of Group IIA of the Periodic Chart, i.e., Be, Mg, Ca, Sr, Ba, Ra and also with ammonium ions. Another technique to reduce acidity is to steam the acidic form of the catalyst at high temperatures, e.g. temperatures of 1000° F. and greater.

A special test has been devised to measure the acidity of various zeolite catalyst components in order to determine whether or not they are operable in the novel process of this invention. The test involves measure of the rate of cyclopropane isomerization and comparing it against 46 A.I. silica-alumina as a reference standard.

The test procedure involves utilizing a 5 to 50 mg sample having a particle size of 20 to 200 mesh and mixing the same with about 1 ml of Vycor chips and loading into a 5 mm inside diameter Vycor reactor tube which is heated in air at a flow rate of 150 ml per minute to 538° C. and maintained there for 30 minutes. The sample is then cooled to 250° C. in helium at a flow rate of 12–80 ml per minute. Cyclopropane (helium/cyclopropane, 4 vol. to vol.) is then introduced and the reactor effluent analyzed by gas chromatographic techniques. The contact time is adjusted to keep the conversion with 0.5 to 50%. Since it is well known in the literature that the isomerization of cyclopropane is first order, rate constants may be determined at several temperatures to check for diffusional limitations. Using the above technique, the first order rate content for the standard 46 A.I. silica-alumina catalyst is 63.3 seconds$^{-1}$ at 250° C. This value was arbitrarily assigned an index of 1,000 so as to serve as a reference value. Thus, the cyclopropane index (C.P.I. Index) for a candidate catalyst component with a first order rate constant of 3.165 would be determined as follows:

$$\frac{1,000 \times 3.165}{63.3} = 50$$

Thus, the expressions "substantially non-acidic" and a zeolite which is "virtually free of acidic sites" as used throughout the specification and claims is intended to define a zeolite which has a C.P.I. Index of no greater than 50, and preferably no greater than 10, as measured by the aforementioned test.

The following Table 1 lists the values obtained when subjecting various zeolites to the cyclopropane isomerization test previously set forth.

| Catalyst Components | Cyclopropane Isomerization (CPI) Index | |
|---|---|---|
| | k,sec$^{-1}$ 250° C. | CPI |
| (1) MgPHZSM-5 | 151 | 2400 |
| (2) 46 A. I. Si/Al, Ref. Std. | 63.3 | 1000 |
| (3) ZrO$_2$ | 60.2 | 950 |
| (4) HZSM-5, SiO$_2$/Al$_2$O$_3$ = 1670 | 50.0 | 790 |
| (5) KHZSM-5 | 3.98 | 63 |
| (6) NaZSM-5, SiO$_2$/Al$_2$O$_3$ = 90 (Bx NaHCO$_3$) | 1.36 | 21 |
| (7) NaHZSM-5, SiO$_2$/Al$_2$O$_3$ = 1670 | 0.441 | 7.0 |
| (8) NaZSM-5, SiO$_2$/Al$_2$O$_3$ = 600 | 0.125 | 2.0 |
| (9) NaZSM-5, SiO$_2$Al$_2$O$_3$ = 1670 | 0.050 | 0.8 |

From the above Table 1, it can be seen that there are ZSM-5 zeolites which have the requisite C.P.I. Index for the novel process of this invention, as well as ZSM-5 type materials in which the C.P.I. Index is so high as to preclude their usefullness herein. Thus, for example, Catalyst Component No. 1 is a magnesium phosphorous exchanged ZSM-5 and, as can be seen, its acidity is higher than the 46 A.I. reference standard. Catalyst Component No. 4 is an acid exchanged ZSM-5 zeolite having a silica-to-alumina mole ratio of 1670 and, as can be seen, this material is also inoperable in the novel process of this invention. Catalyst Component No. 5 is a potassiumn exchanged acid ZSM-5, but it simply has not been exchanged with enough potassium to lower its acidity since it has a C.P.I. Index of 63. Catalyst Components 6, 7, 8 and 9 all possess a sufficiently low C.P.I. Index to be potential candidates for the novel process of this invention, providing of course that the appropriate metal component is intimately combined with a substantially non-acidid zeolite according to this invention.

From the foregoing it is evident that in order to attain the requisite state of non-acidity, more than one of the aforementioned techniques may have to be applied. Thus it may not be sufficient that a high silica zeolite, e.g., SiO$_2$/Al$_2$O$_3$=1600, is utilized, such zeolite may still have to undergo base exchange or steaming. Alternatively, the extensive base exchange of a low silica-alumina zeolite, or the use of a ultra high-silica zeolite, e.g., SiO$_2$/Al$_2$O$_3$=30,000, may result in a material having the requisite C.P.I. value without any further treatment.

A major difference between the instant invention and the heretofore practiced processes for synthesis gas conversion utilizing zeolites resides in the fact that the specific products obtainable from the present invention will not be generated by a mere physical mixture of a member of the novel class of zeolites and the useful metal. The metal must be intimately combined with the zeolite. In this connection, methods for including such metals within the pores of zeolites to arrive at an intimate combination are known in the art. The preferred technique for achieving such intimate combination is impregnation of the zeolite with an aqueous solution of a salt of the desired metal. The nature of the salt is not critical and any water-soluble salt such as chloride, sulfate and nitrate can be utilized. The zeolite may be soaked or dipped in such a salt solution, or alternatively, the solution can be vacuum sprayed onto the zeolite. The amount of metal in said zeolite can range from between about 0.1 and about 10 wt. percent, preferably from between about 0.2 and about 5 wt. percent.

The useful metal component of the catalyst of this invention is selected from the group consisting of rhodium, platinum, palladium and iridium, the preferred metal component is rhodium.

The catalyst of this invention may be prepared in various ways. The catalyst may be prepared in the form of catalyst particles such as pellets or extrudates. The particle size of the individual component particles may be quite small, for example from about 20 to about 150 microns, when intended for use in fluid bed operation; or they may be as large as up to about ½ inch for fixed bed operation. Binders such as clays may be added. The component that has catalytic activity for the reduction of carbon monoxide is formed on the zeolite component by conventional means such as impregnation of that solid with salt solutions of the desired metals, followed by spray drying and calcination.

In the process of this invention, synthesis gas is contacted with the catalyst of this invention at a temperature of between about 500° F. and about 1000° F., preferably from between about 700° F. to 900° F.; at a pressure of from between about 10 and about 200 atmospheres, preferably from between about 60 and about 100 atmospheres; and at a gas hourly space velocity (GHSV) from between about 100 and about 10,000 volumes of gas, at standard temperature and pressure per volume of catalyst, preferably from between about 200 and about 2,000 GHSV. The catalyst may be contained in a fixed bed, or a fluidized bed may be used. The product stream containing hydrocarbons, oxygenates, unreacted gases and steam may be cooled and the hydrocarbons and oxygenates recovered by any of the techniques known in the art, which techniques do not constitute part of this invention. The recovered hydrocarbons and oxygenates may be further separated by distillation or other means to recover one or more products such as high octane gasoline or chemical intermediates.

The concepts and objectives of the present invention are further supported by the following examples.

EXAMPLE 1

This example illustrates the preparation of highly siliceous ZSM-5. The synthesis of this zeolite involved the combining of four major components-silicate solution, acid solution, additional solids and additional liquid.

The silicate solution was comprised of 1 part Q-brand sodium silicate (PQ Company, Philadelphia, Pa.), 0.58 parts water and 0.0029 parts Daxad 27 (W. R. Grace Company). The acid solution was composed of 0.10 parts sulfuric acid, 0.045 parts sodium chloride, 0.16 parts water and 0.56 parts of prereacted organics.

The prereacted organics were prepared by charging the following materials to an autoclave: 0.30 parts methylethyl ketone, 0.18 parts tri-n-propylamine and 0.15 parts n-propyl bromide. These materials for the preparation of the prereacted organics were mixed with gentle agitation for 15 minutes. The agitation was stopped and 1 part water was charged to the autoclave. The autoclave was sealed and heated to 220° F. and held at 220° F. for 15 hours. After this reaction period the temperature was raised to 320° F. and the unreacted organics were flashed off. The aqueous phase was removed containing the prereacted organics and contained 1.44% wt nitrogen.

The additional solids for this preparation was 0.14 parts sodium chloride and the additional liquid was 0.029 parts water.

The silicate solution and acid solution were mixed in a mixing nozzle to form a gel which was discharged into an autoclave to which 0.029 parts water had been previously added. The gel was whipped by agitation and 0.14 parts NaCl were added and thoroughly blended. The autoclave was sealed and heated to about 220° F. with agitation at 90 rpm and held for 54.3 hours until crystallization was complete. The contents of the autoclave were cooled and discharged. The crystallized product was analyzed by x-ray diffraction and was found to be 100% wt ZSM-5. The chemical analysis of the thoroughly washed crystalline product is

|  | % Wt | Mole Ratio |
|---|---|---|
| $Al_2O_3$ | 0.10 | 1.0 |
| $SiO_2$ | 98.3 | 1670 |
| Na | 1.6 | — |
| $Na_2O$ | — | 35.5 |
| N (as received basis) | 0.75 | 63.9 |
| C (as received basis) | 8.98 | 892 |

EXAMPLE 2

Highly siliceous Na ZSM-5 with a silica to alumina mole ratio of about 1600 and impregnated with 0.5 wt. percent rhodium (as nitrate) is representative of a catalyst useful in the instant invention. This catalyst was prepared by dissolving 0.14 grams of rhodium nitrate salt in 15 ml of water and contacting the resultant solution with 10 grams of highly siliceous Na ZSM-5 prepared according to Example 1 under vacuum conditions. The sample was then vacuum-dried in a rotary evaporator at a temperature of about 90° C. and further subjected to calcination at 538° C. for 10 hours in an oven. The impregnated Na ZSM-5 was then reduced at 195° C. at 1 atmosphere pressure and for 4½ hours with 30 cc/minute of flowing hydrogen.

EXAMPLE 3

The catalyst prepared according to Example 2 was tested for synthesis gas conversion conducted at 800° F., 1400 psig and 600 GHSV in a fixed bed reactor with 2.93 grams of catalyst. The synthesis gas composition was 50 vol.% CO, and 50 vol.% $H_2$. Gas and liquid products were separated and analyzed chromatographically. The results are shown in Table 2.

TABLE 2

| *Conversion to Products: 56% | |
|---|---|
| Product Breakdown: | 74% Hydrocarbons |
|  | 26% Oxygenates |
| Product was shape-selective, i.e., virtually free of $C_{11+}$ compounds. | |
| Composition of Oxygenates; | wt. % |
| Methanol | 12 |
| Ethanol | 25 |
| $C_{3+}$ Alcohols | 12 |
| Aldehydes | 28 |
| Ketones | 2 |
| Esters | 6 |
| Acetic Acid | 5 |
| Other | 10 |
|  | 100 |
| Composition of Hydrocarbons: | wt. % |
| $C_1$ | 45.3 |
| $C_2$ | 24.4 |
| $C_3$ | 18.2 |

TABLE 2-continued

| | |
|---|---|
| $C_4$ | 7.4 |
| $C_5$ | 1.6 |
| $C_6$ to $C_{10}$ | 2.9 |
| $C_{11+}$ | 0.2 |

*Conversion = $\frac{\text{Carbon in Products}}{\text{Carbon in Feed}} \times 100$ Having thus generally described the method, catalysts and concepts of the present invention and presented examples in support thereof, it is to be understood that no undue restrictions are to be imposed by reason thereof except as defined by the claims.

What is claimed is:

1. A catalyst composition for use in converting synthesis gas into oxygenate-containing mixtures, which comprises a zeolite which is virtually free of acid sites and which has an acid activity, as measured by the C.P.I. Index, of no greater than 50, and characterized by a silica to alumina mole ratio of at least about 12, a constraint index within the range of 1 to 12, having intimately combined therewith a metal selected from the group consisting of rhodium, platinum, palladium and iridium.

2. A catalyst composition according to claim 1 wherein said acid activity, as measured by the C.P.I. Index, is no greater than 10.

3. A catalyst composition according to claim 1 wherein said zeolite is selected from the group consisting of ZSM-5, ZSM-11, ZSM-12, ZSM-23, ZSM-35 and ZSM-38.

4. A catalyst composition according to claim 3 wherein said zeolite is ZSM-5.

5. A catalyst composition according to claim 1 wherein said metal is rhodium.

6. A catalyst composition according to claim 1 wherein said metal is impregnated in said zeolite.

7. A catalyst composition according to claim 1 wherein said zeolite is rendered virtually free of acid sites by base exchange of an acidic zeolites.

8. A catalyst composition according to claim 7 wherein said base exchange is carried out with cations selected from the group consisting of metals from Group IA of the Periodic Chart, Group IIA of the Periodic Chart and ammonium cations.

9. A catalyst composition according to claim 8 wherein said Group IA cation is a sodium cation.

10. A catalyst composition according to claim 1 wherein said zeolite is highly siliceous and sodium exchanged.

11. A catalyst composition according to claim 1 wherein said metal intimately combined with said zeolite is in the range of from about 0.1 to about 10 weight percent of the total composition.

12. A catalyst composition according to claim 11 wherein said metal is in the range of from about 0.2 to about 5 weight percent of the total composition.

* * * * *